US010906865B2

(12) United States Patent
Iida et al.

(10) Patent No.: US 10,906,865 B2
(45) Date of Patent: Feb. 2, 2021

(54) METHOD FOR PRODUCING 1,4-DICYANOCYCLOHEXANE, 1,4-BIS(AMINOMETHYL)CYCLOHEXANE AND 1,4-CYCLOHEXANEDICARBOXYLIC ACID

(71) Applicant: Mitsubishi Gas Chemical Company, Inc., Chiyoda-ku (JP)

(72) Inventors: Akifumi Iida, Niigata (JP); Yuta Ohmori, Niigata (JP); Emi Nakano, Niigata (JP); Aoi Yamazoe, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/337,262

(22) PCT Filed: Sep. 28, 2017

(86) PCT No.: PCT/JP2017/035164
§ 371 (c)(1),
(2) Date: Mar. 27, 2019

(87) PCT Pub. No.: WO2018/066447
PCT Pub. Date: Apr. 12, 2018

(65) Prior Publication Data
US 2019/0225572 A1    Jul. 25, 2019

(30) Foreign Application Priority Data
Oct. 4, 2016  (JP) ................. 2016-196518

(51) Int. Cl.
| C07C 211/18 | (2006.01) |
| C07C 209/46 | (2006.01) |
| C07C 209/48 | (2006.01) |
| C07C 253/22 | (2006.01) |
| C07C 255/46 | (2006.01) |
| C07C 51/36  | (2006.01) |
| C07C 61/09  | (2006.01) |
| C07B 61/00  | (2006.01) |

(52) U.S. Cl.
CPC ............ *C07C 209/46* (2013.01); *C07C 51/36* (2013.01); *C07C 61/09* (2013.01); *C07C 209/48* (2013.01); *C07C 211/18* (2013.01); *C07C 253/22* (2013.01); *C07C 255/46* (2013.01); *C07B 61/00* (2013.01)

(58) Field of Classification Search
CPC ... C07C 211/18; C07C 209/46; C07C 209/48; C07C 253/22; C07C 255/46; C07C 51/36; C07C 61/09; C07B 61/00
See application file for complete search history.

(56) References Cited

U.S. PATENT DOCUMENTS 8,865,938 B2 * 10/2014 Yoshimura ............ C07C 253/22
564/448
2010/0216905 A1   8/2010 Kuwamura et al.
2013/0197270 A1   8/2013 Yoshimura et al.

FOREIGN PATENT DOCUMENTS

| CN | 101591237 A | * | 12/2009 |
| CN | 101591237 A |   | 12/2009 |
| CN | 105016942 A |   | 11/2015 |
| CN | 105016943 A |   | 11/2015 |
| CN | 105016944 A | * | 11/2015 |
| CN | 105016944 A |   | 11/2015 |
| JP |   5562429 B2 |   | 7/2014  |
| JP |   5640093 B2 |   | 10/2014 |
| WO | WO 2009/051114 A1 | | 4/2009 |

OTHER PUBLICATIONS

CN105016944A-partial-translation, 2020, partial oral/written translation of relevant parts of the document.*
CN101591237-partial-translation, 2020, partial oral/written translation of relevant parts of the document.*
International Search Report dated Dec. 26, 2017 in PCT/JP2017/035164 filed Sep. 28, 2017.
Prince, F. R. et al., "Cis/Trans Coplyamides of 1,4-Bisaminomethylcyclohexane," Journal of Polymer Science: Part A-1, vol. 10, 1972, pp. 465-470.
Ronbunshu, K., Japanese Journal of Polymer Science and Technology, vol. 36. No. 5, 1979, pp. 305-310.

* cited by examiner

*Primary Examiner* — Sun Jae Yoo
(74) *Attorney, Agent, or Firm* — Oblon, McClelland, Maier & Neustadt, L.L.P.

(57) ABSTRACT

A method for producing 1,4-dicyanocyclohexane, having a step of obtaining 1,4-dicyanocyclohexane by subjecting a heated concentrate of an aqueous ammonia solution of 1,4-cyclohexanedicarboxylic acid to a cyanation reaction.

10 Claims, No Drawings

METHOD FOR PRODUCING 1,4-DICYANOCYCLOHEXANE, 1,4-BIS(AMINOMETHYL)CYCLOHEXANE AND 1,4-CYCLOHEXANEDICARBOXYLIC ACID

TECHNICAL FIELD

The present invention relates to a method for producing 1,4-dicyanocyclohexane, 1,4-bis(aminomethyl)cyclohexane and 1,4-cyclohexanedicarboxylic acid.

BACKGROUND ART

Bis(aminomethyl)cyclohexane is an industrially important compound, which is used as a raw material for an epoxy curing agent, polyamide, polyurethane, etc. Bis(aminomethyl)cyclohexane has two isomers: cis-isomer and trans-isomer, resulting from cyclohexane ring. For polymers for which bis(aminomethyl)cyclohexane is used, it is known that the physical properties are significantly changed depending on the isomeric ratio between cis-isomer and trans-isomer.

For example, regarding polyamide for which 1,4-bis (aminomethyl)cyclohexane is used, it is known that the higher the content rate of trans-isomer is, the higher the melting point and the thermal resistance becomes (Non Patent Document 1). In addition, regarding polyurethane for which 1,4-bisisocyanatomethylcyclohexane derived from 1,4-bis(aminomethyl)cyclohexane is used, it is known that the higher the content rate of trans-isomer is, the more the requisite physical properties depending on various applications improve (Patent Document 1).

As a synthetic method for such bis(aminomethyl)cyclohexane, a method described in Patent Document 2 is known. According to Patent Document 2, with the intention of providing a production method for trans-1,4-bis(aminomethyl)cyclohexane that is excellent in terms of facility, safety and economy, a production method for trans-1,4-bis(aminomethyl)cyclohexane, including: a nucleus hydrogenation step of nucleus-hydrogenating at least one of terephthalic acid or a derivative thereof selected from the group consisting of terephthalic acid, terephthalic acid ester and terephthalamide to obtain hydrogenated terephthalic acid or a derivative thereof; a cyanation step of contacting the hydrogenated terephthalic acid or a derivative thereof obtained via the nucleus hydrogenation step with ammonia to obtain 1,4-dicyanocyclohexane and obtaining trans-1,4-dicyanocyclohexane from the obtained 1,4-dicyanocyclohexane; and an aminomethylation step of contacting the trans-1,4-dicyanocyclohexane obtained via the cyanation step with hydrogen to obtain trans-1,4-bis(aminomethyl)cyclohexane, characterized in that a metal oxide is used as a catalyst in the cyanation step and the metal content rate of the obtained trans-1,4-dicyanocyclohexane is not more than 3000 ppm is proposed.

CITATION LIST

Patent Document

Patent Document 1
International Publication No. WO 2009/051114
Patent Document 2
Japanese Patent No. 5562429

Non Patent Document

Non Patent Document 1
J. Polym. Sci. Part A-1, 10, 465 (1972)

Non Patent Document 2
Japanese Journal of Polymer Science and Technology Vol. 65, No. 5, pp. 305-310 (1979)

SUMMARY OF INVENTION

Technical Problem

In the production method described in Patent Document 2, it is explained that 1,4-dicyanocyclohexane used for producing trans-1,4-bis(aminomethyl)cyclohexane is obtained by contacting the hydrogenated terephthalic acid or a derivative thereof with ammonia. More particularly, according to examples in Patent Document 2, by contacting 1,4-cyclohexanedicarboxylic acid with ammonia gas and making them react at 280° C., 1,4-dicyanocyclohexane is obtained.

However, in the method described in Patent Document 2, it is necessary to introduce the whole amount of the ammonia gas used for the method from outside the system, and thus, there is room for further improvement from the viewpoint of effectively utilizing ammonia.

The present invention has been made in light of the circumstances described above, and an object is to provide a new method for producing 1,4-dicyanocyclohexane that preferably enables effective utilization of ammonia. Furthermore, an object of the present invention is to provide a method for producing 1,4-bis(aminomethyl)cyclohexane using 1,4-dicyanocyclohexane obtained via the method, and a method for producing 1,4-cyclohexanedicarboxylic acid, which is a raw material for 1,4-dicyanocyclohexane.

Solution to Problem

The present inventors have made diligent researches in order to achieve the objects described above, and consequently have found that ammonia can be utilized effectively by using ammonia that is subjected to the reaction with 1,4-dicyanocyclohexane in an aspect different from that described in Patent Document 2, and have achieved the present invention.

Namely, the present invention is as follows:

[1] A method for producing 1,4-dicyanocyclohexane, having a step of obtaining 1,4-dicyanocyclohexane by subjecting a heated concentrate of an aqueous ammonia solution of 1,4-cyclohexanedicarboxylic acid to a cyanation reaction.

[2] The method according to [1], further having a step of obtaining the 1,4-cyclohexanedicarboxylic acid by subjecting terephthalic acid in an aqueous ammonia solution to a hydrogenation reaction.

[3] The method according to [2], wherein at least a part of an aqueous ammonia solution included in a reaction solution after the step of obtaining 1,4-cyclohexanedicarboxylic acid is used as the aqueous ammonia solution in the step of obtaining 1,4-dicyanocyclohexane.

[4] The method according to [2] or [3], wherein the reaction solution after the step of obtaining 1,4-cyclohexanedicarboxylic acid is used as a raw material solution for the step of obtaining 1,4-dicyanocyclohexane, without collecting 1,4-cyclohexanedicarboxylic acid by filtration therefrom.

[5] The method according to any one of [1] to [4], further having a step of obtaining the heated concentrate by heating the aqueous ammonia solution of 1,4-cyclohexanedicarboxylic acid to 100 to 200° C. to remove at least a part of water.

[6] A method for producing 1,4-bis(aminomethyl)cyclohexane, having a step of obtaining 1,4-bis(aminomethyl)

cyclohexane by subjecting 1,4-dicyanocyclohexane obtained via the method according to any one of [1] to [5] to a hydrogenation reaction.

[7] A method for producing 1,4-cyclohexanedicarboxylic acid, having a step of obtaining 1,4-cyclohexanedicarboxylic acid by subjecting terephthalic acid in an aqueous ammonia solution to a hydrogenation reaction.

Advantageous Effects of Invention

According to the present invention, a new method for producing 1,4-dicyanocyclohexane can be provided that enables effective utilization of ammonia. Moreover, according to the present invention, a method for producing 1,4-bis(aminomethyl)cyclohexane using 1,4-dicyanocyclohexane obtained via the method described above, and a method for producing 1,4-cyclohexanedicarboxylic acid, which is a raw material for 1,4-dicyanocyclohexane can also be provided.

DESCRIPTION OF EMBODIMENT

Hereinafter, an embodiment for performing the present invention (hereinafter, simply referred to as a "present embodiment") will be described in detail, but the present invention is not limited to the present embodiment described below. It is possible to make various modifications to the present invention within a range of not departing from its spirit.

A method for producing 1,4-dicyanocyclohexane of the present embodiment (hereinafter, also referred to as a "1,4-CHDN production method") has a step (hereinafter, also simply referred to as a "cyanation step") of obtaining 1,4-dicyanocyclohexane by subjecting a heated concentrate of an aqueous ammonia solution of 1,4-cyclohexanedicarboxylic acid to a cyanation reaction. By using the heated concentrate for the cyanation step, the yield of 1,4-dicyanocyclohexane can be increased compared to the case where, for example, cyanation is performed only by introducing ammonia gas into the system. The main cause is believed to be, without being limited to, that the heating at the temperature described above produces an intermediate in the heated concentrate and this intermediate contributes to the cyanation reaction.

1,4-Cyclohexanedicarboxylic acid used as a raw material in the cyanation step may be produced according to an ordinary method, or may be commercially obtained. However, it is preferable that 1,4-cyclohexanedicarboxylic acid be obtained by subjecting terephthalic acid in an aqueous ammonia solution to a hydrogenation reaction. That is, it is preferable that the 1,4-CHDN production method of the present embodiment have a step (hereinafter, also simply referred to as a "nucleus hydrogenation step") of obtaining 1,4-cyclohexanedicarboxylic acid by subjecting terephthalic acid in an aqueous ammonia solution to a hydrogenation reaction (hereinafter, also simply referred to as a "nucleus hydrogenation reaction"). When the 1,4-CHDN production method has the nucleus hydrogenation step, at least a part of an aqueous ammonia solution included in a reaction solution after this step can be used as the aqueous ammonia solution in the cyanation step. Accordingly, the effective utilization of ammonia is also enabled.

In the nucleus hydrogenation step, for example, a catalyst and water are charged into a reactor at first; hydrogen gas is then introduced into the reactor until reaching a predetermined pressure; the suspension is heated and stirred while maintaining the pressure; and the catalyst is reduced to be activated. As to the catalyst, for example, a catalyst used for an ordinary nucleus hydrogenation reaction can be employed, and more particularly, one or two or more metal catalysts, preferably precious metal catalysts, such as Ru, Pd, Pt and Rh, can be used. The catalyst may be those in which the metal catalyst described above as an active component is supported on one or two or more supports that are ordinarily used, such as carbon, $Al_2O_3$, $SiO_2$, $SiO_2$—$Al_2O_3$, $TiO_2$ and $ZrO_2$. When a support is used, the amount of the metal catalyst supported, which is an active component, is preferably 0.1 to 10% by mass based on 100% by mass of the support.

In addition, the pressure in the system upon the activation of the catalyst may be an ordinary pressure (the gas phase part is purged with hydrogen) or may be pressurized. When pressurized, the pressure in the system is preferably 0.1 to 8 MPa, and hydrogen gas may be appropriately introduced into the reactor in order to maintain such pressure. Furthermore, the activation temperature is preferably 50 to 250° C. By making conditions upon the activation of the catalyst within the ranges described above, the catalyst can be activated further more effectively and reliably. In addition, the stirring time may be any length as long as it is sufficient for activating the catalyst.

Next, the reactor is cooled and the hydrogen gas remaining in the system is discharged to outside the system; terephthalic acid and an aqueous ammonia solution are then charged into the reactor; and furthermore, hydrogen gas is introduced until reaching a predetermined pressure. Upon this, the amount of the terephthalic acid charged is preferably 2 to 20% by mass based on the entire reaction solution. In addition, the amount of the aqueous ammonia solution charged is preferably an amount that provides 200 to 400 mol % of ammonia based on 100 mol % of terephthalic acid. There is no limitation on the amount of the catalyst used, and it may be appropriately determined to achieve the target reaction time, considering the content of the supported metal catalyst and the amount of terephthalic acid used for the reaction. By using each raw material, etc. in an amount within the ranges described above, the yield and selectivity of the obtained 1,4-cyclohexanedicarboxylic acid can be enhanced.

Next, the inside of the reactor is heated to a predetermined temperature to proceed with the nucleus hydrogenation reaction. The reaction temperature upon this is preferably 40 to 150° C., and the reaction pressure is preferably 0.5 to 15 MPa in terms of the hydrogen partial pressure. Note that the reaction time may be any length as long as it is long enough for the nucleus hydrogenation reaction to proceed sufficiently. By adjusting the reaction conditions to be within the ranges mentioned above, the yield and selectivity of the obtained 1,4-cyclohexanedicarboxylic acid can be enhanced. In addition, hydrogen gas may be appropriately introduced into the reactor in order to maintain the reaction pressure within the range described above.

When 1,4-cyclohexanedicarboxylic acid is produced in a manner mentioned above, the reaction solution includes an aqueous ammonia solution and the produced 1,4-cyclohexanedicarboxylic acid. The 1,4-CHDN production method of the present embodiment can use at least a part of the aqueous ammonia solution as the aqueous ammonia solution in the cyanation step, along with 1,4-cyclohexanedicarboxylic acid produced in the nucleus hydrogenation step. By doing this, the effective utilization of ammonia is enabled. Among the ammonia in the reaction solution after the nucleus hydrogenation step, preferably 5 to 25% by mass of the ammonia can be used in the cyanation step.

In addition, it is preferable to use the reaction solution after the nucleus hydrogenation step as a raw material solution for the cyanation step, without collecting 1,4-cyclohexanedicarboxylic acid by filtration therefrom. By doing this, a filtration step can be omitted, thereby shortening the time from the nucleus hydrogenation step to the cyanation step, which enables reduction of labor and costs.

It is preferable for the 1,4-CHDN production method of the present embodiment to have, prior to the cyanation step, a step (hereinafter, also simply referred to as a "heat concentration step") of obtaining the heated concentrate described above by heating the aqueous ammonia solution of 1,4-cyclohexanedicarboxylic acid (that is, the aqueous ammonia solution including 1,4-cyclohexanedicarboxylic acid) to remove at least a part of water. In the heat concentration step, the concentration of 1,4-cyclohexanedicarboxylic acid in the aqueous ammonia solution is preferably 25 to 50 mol % based on 100 mol % of ammonia. In addition, in the heat concentration step, the concentration of ammonia in the initial aqueous ammonia solution is preferably 0.1 to 10% by mass based on the whole amount of the aqueous ammonia solution. Furthermore, the heating temperature upon obtaining the heated concentrate is preferably 70° C. to 200° C., and the pressure may be an ordinary pressure or may be pressurized. The heating temperature may also be 100° C. to 170° C.

By adjusting the concentration of each component and heating conditions to be within the ranges described above, the yield of 1,4-dicyanocyclohexane in the cyanation step is further increased. Particularly, the heating temperature within a range of 100° C. to 200° C. is preferred from the viewpoint of producing the heated concentrate by removing water via volatilization from the aqueous ammonia solution. Furthermore, it is more preferable that the heating temperature be within a range of 100° C. to 170° C. In addition, in the present embodiment, the use of the heated concentrate described above for the cyanation step is useful in that ammonia present in the heated concentrate can be used effectively as a raw material for the cyanation reaction.

The heat concentration step may be performed sequentially with the subsequent cyanation step. That is, an aqueous ammonia solution of 1,4-cyclohexanedicarboxylic acid, water as necessary, and a catalyst are charged into a reactor at first; and an inert gas is introduced until the pressure in the system reaches a predetermined pressure, optionally along with ammonia gas as necessary. Then, in order to maintain the pressure in the reactor within a constant range while retaining the temperature in the reactor within a range of preferably 100° C. to 200° C., the inert gas is introduced into the reactor or the gas in the reactor is discharged, appropriately, thereby obtaining a heated concentrate. After this, the cyanation reaction may be proceeded by introducing ammonia gas into the reactor as necessary and adjusting the temperature and pressure in the reactor to be a temperature and pressure required for the cyanation step. In this case, it is preferable to set an occasion to introduce ammonia gas after obtaining the heated concentrate because by doing this, ammonia can be utilized more efficiently. Examples of the inert gas described above include, for example, nitrogen gas, as well as noble gases, such as argon and helium. However, the inert gas does not have to be introduced into the system.

In the cyanation step, the heated concentrate of the aqueous ammonia solution of 1,4-cyclohexanedicarboxylic acid, water as necessary, and a catalyst are charged into a reactor at first; and an inert gas is introduced until the pressure in the system reaches a predetermined pressure. Then, the inside of the reactor is heated to a predetermined temperature, and the inert gas is appropriately introduced into the reactor in order to maintain the pressure in the reactor within a constant range while stirring the inside of the reactor, thereby advancing the cyanation reaction.

As to the catalyst, a catalyst used for an ordinary cyanation reaction can be employed, and more particularly, examples of the catalyst include silica gel, alumina, silica alumina, zinc oxide, tin oxide, iron oxide, titanium oxide, zirconium oxide and cobalt oxide. Among these, zinc oxide and tin oxide are preferred from the viewpoint of advancing the cyanation reaction more effectively and reliably. These catalysts are used singly or in combinations of two or more. Furthermore, the amount of the catalyst used is preferably 0.5 to 20% by mass based on 100% by mass of 1,4-cyclohexanedicarboxylic acid. By using the catalyst in an amount within the range described above, the yield and selectivity of the obtained 1,4-dicyanocyclohexane can be enhanced.

In addition, ammonia gas may be introduced into the reactor appropriately. The amount of the ammonia gas used is preferably 200 to 1000 mol % based on 100 mol % of 1,4-cyclohexanedicarboxylic acid. Accordingly, the yield and selectivity of the obtained 1,4-dicyanocyclohexane can be enhanced.

In the cyanation step, the concentration of 1,4-cyclohexanedicarboxylic acid in the aqueous ammonia solution is preferably 100 to 1000 mol % based on 100 mol % of ammonia. In addition, in the cyanation step, the concentration of ammonia in the aqueous ammonia solution is preferably 0.1 to 10% by mass based on the whole amount of the aqueous ammonia solution.

The reaction temperature in the cyanation step is preferably 270 to 320° C., and the reaction pressure may be an ordinary pressure or may be pressurized. Note that the reaction time may be any length as long as it is long enough for the cyanation reaction to proceed sufficiently. By adjusting the concentration of each raw material and the reaction conditions to be within the ranges mentioned above, the yield and selectivity of the obtained 1,4-dicyanocyclohexane can be enhanced.

1,4-Dicyanocyclohexane may be collected by distilling the reaction solution including 1,4-dicyanocyclohexane thus obtained, as necessary (hereinafter, this step is referred to as a "distillation step"). The distillation is performed by, for example, heating a distillation apparatus from the bottom section such that the pressure in the system in the distillation apparatus is 3.0 kPa to 4.0 kPa and the temperature is 180 to 230° C., and by cooling the top section, thereby performing gas-liquid contact in the apparatus. By doing this, 1,4-dicyanocyclohexane can be selectively drawn and collected from the top section of the distillation apparatus.

A method for producing 1,4-bis(aminomethyl)cyclohexane of the present embodiment has a step (hereinafter, also simply referred to as a "nitrile hydrogenation step") of obtaining 1,4-bis(aminomethyl)cyclohexane by subjecting the obtained 1,4-dicyanocyclohexane as mentioned above to a hydrogenation reaction (hereinafter, also referred to as a "nitrile hydrogenation reaction").

In the nitrile hydrogenation step, 1,4-dicyanocyclohexane, a solvent, and a catalyst are charged into a reactor at first; and hydrogen gas is introduced until the pressure in the system reaches a predetermined pressure. Then, the inside of the reactor is heated to a predetermined temperature, and hydrogen gas is appropriately introduced into the reactor in order to maintain the pressure in the reactor within a constant range, thereby advancing the nitrile hydrogenation reaction.

As to the solvent, a solvent used for an ordinary nitrile hydrogenation reaction can be employed, and more particularly, examples of the solvent include alcohols, such as methanol, ethanol, 1-propanol, 2-propanol, 1-butanol, 2-butanol and tert-butanol; aromatic hydrocarbons, such as meta-xylene, mesitylene and pseudocumene; liquid ammonia; and aqueous ammonia. These solvents are used singly or in combinations of two or more. In addition, as to the catalyst, for example, a catalyst used for an ordinary nitrile hydrogenation reaction can be employed, and more particularly, a catalyst containing Ni and/or Co can be used. Generally, as to the catalyst, a catalyst made by making Ni and/or Co support onto $Al_2O_2$, $SiO_2$, diatomaceous earth, $SiO_2$—$Al_2O_3$ or $ZrO_2$ by a precipitation method, Raney nickel, or Raney cobalt is suitably used. Among these, the Raney cobalt catalyst and Raney nickel catalyst are preferred from the viewpoint of advancing the nitrile hydrogenation reaction more effectively and reliably. These catalysts are used singly or in combinations of two or more. Furthermore, the amount of the catalyst used is preferably 0.1 to 150% by mass, more preferably 0.1 to 20% by mass, and further preferably 0.5 to 15% by mass based on 100% by mass of 1,4-CHDN. By using the catalyst in an amount within the range described above, the yield and selectivity of the obtained 1,4-bis(aminomethyl)cyclohexane can be enhanced.

The concentration of 1,4-dicyanocyclohexane in the nitrile hydrogenation step is preferably 1 to 50% by mass and more preferably 2 to 40% by mass based on the whole amount of the reaction solution from the viewpoint of reaction efficiency. In addition, the reaction temperature in the nitrile hydrogenation step is preferably 40 to 150° C., and the reaction pressure is preferably 0.5 to 15 MPa in terms of the hydrogen partial pressure. Note that the reaction time may be any length as long as it is long enough for the nitrile hydrogenation reaction to proceed sufficiently. By adjusting the reaction conditions to be within the ranges mentioned above, the yield and selectivity of the obtained 1,4-bis(aminomethyl)cyclohexane can be enhanced.

The production method of the present embodiment is useful in that the use of the heated concentrate described above for the cyanation step consequently allows ammonia present in the heated concentrate to be used effectively as a raw material for the cyanation reaction. In addition, by using the heated concentrate for the cyanation step, the selectivity and yield of 1,4-dicyanocyclohexane can be enhanced compared to the case where, for example, cyanation is performed only by introducing ammonia gas into the system. Furthermore, when the 1,4-CHDN production method has the nucleus hydrogenation step, at least a part of the aqueous ammonia solution included in the reaction solution after this step can be used as the aqueous ammonia solution in the cyanation step. Accordingly, the effective utilization of ammonia is enabled. In addition, when the reaction solution after the nucleus hydrogenation step is used as a raw material solution for the cyanation step, without collecting 1,4-cyclohexanedicarboxylic acid by filtration therefrom, a filtration step can be omitted, thereby shortening the time from the nucleus hydrogenation step to the cyanation step, which enables reduction of labor and costs. Moreover, in the production method of the present embodiment, it is also advantageous that compounds produced in each step have relatively low melting points and thus tend to provide excellent handleability and solubility in a solvent.

EXAMPLE

Hereinafter, the present invention will be further described in detail with reference to Examples, but the present invention is not limited to these Examples.

Nucleus Hydrogenation Step

Synthetic Example 1-1

At first, in a 200 mL pressure resistant vessel made of SUS316, 1.06 g (0.5 g on dried basis) of 5% Ru/C catalyst (manufactured by N.E. CHEMCAT CORPORATION, type A, water content: 52.8% by mass) as a catalyst and 48 g of water were charged; hydrogen gas was then introduced into the vessel until the pressure reached 1 MPa; the mixture was heated at 150° C. and stirred; and the catalyst was reduced to be activated. Next, the vessel was cooled and the hydrogen gas remaining in the system was discharged to outside the system; 5.00 g (0.030 mol) of terephthalic acid (reagent manufactured by Tokyo Chemical Industry Co., Ltd.) and 5.50 g of 28% aqueous ammonia solution (manufactured by Wako Pure Chemical Industry Co., Ltd.) were then charged into the vessel; and furthermore, hydrogen gas was introduced until reaching a reaction pressure of 8 MPa. Next, the inside of the vessel was heated to a reaction temperature of 80° C., and while retaining the constant temperature and stirring the inside of the vessel with an electromagnetic stirring blade at 750 rpm, the nucleus hydrogenation reaction was proceeded for 60 minutes.

After the reaction finished, the catalyst in the reaction solution was removed by filtration, and the reaction solution was analyzed by HPLC (product name "Prominence" manufactured by Shimadzu Corporation; column: model name "KC-811" from Shodex; conditions: eluent: 0.1 mass % aqueous phosphoric acid, flow rate 0.7 mL/min, column temperature 50° C., photodiode array detector). As a result, the conversion rate of terephthalic acid was 99.9%, the selectivity and the yield of 1,4-cyclohexanedicarboxylic acid were 97.7% and 97.6%, respectively.

Synthetic Example 1-2

The nucleus hydrogenation reaction was proceeded in a similar manner as Synthetic Example 1-1 except that the reaction temperature was changed from 80° C. to 90° C. The conversion rate of terephthalic acid was 100.0%, the selectivity and the yield of 1,4-cyclohexanedicarboxylic acid were 97.3% and 97.3%, respectively.

Synthetic Example 1-3

The nucleus hydrogenation reaction was proceeded in a similar manner as Synthetic Example 1-1 except that the reaction temperature was changed from 80° C. to 60° C. The conversion rate of terephthalic acid was 99.3%, the selectivity and the yield of 1,4-cyclohexanedicarboxylic acid were 97.1% and 96.4%, respectively.

Synthetic Example 1-4

The nucleus hydrogenation reaction was proceeded in a similar manner as Synthetic Example 1-1 except that the reaction pressure was changed from 8 MPa to 5 MPa. The conversion rate of terephthalic acid was 100%, the selectivity and the yield of 1,4-cyclohexanedicarboxylic acid were 97.7% and 97.7%, respectively.

Synthetic Example 1-5

The nucleus hydrogenation reaction was proceeded in a similar manner as Synthetic Example 1-1 except that the reaction pressure was changed from 8 MPa to 3 MPa. The conversion rate of terephthalic acid was 99.9%, the selectivity and the yield of 1,4-cyclohexanedicarboxylic acid were 97.1% and 97.1%, respectively.

Synthetic Example 1-6

The nucleus hydrogenation reaction was proceeded in a similar manner as Synthetic Example 1-1 except that the catalyst was changed from 1.06 g of 5% Ru/C catalyst to 0.50 g of 5% $Ru/Al_2O_3$ catalyst (manufactured by N.E. CHEMCAT CORPORATION). The conversion rate of terephthalic acid was 99.9%, the selectivity and the yield of 1,4-cyclohexanedicarboxylic acid were 96.0% and 96.0%, respectively.

Heat Concentration Step and Cyanation Step

Synthetic Example 2-1

In a 100 mL four neck flask equipped with a stirring blade, a gas introduction tube, a thermocouple and a dehydration apparatus, 30.0 g (0.174 mol) of 1,4-cyclohexanedicarboxylic acid, 23.36 g of 28% aqueous ammonia solution (manufactured by Wako Pure Chemical Industry Co., Ltd.), 0.24 g of zinc oxide (manufactured by Kanto Chemical Co., Inc.) as a catalyst and 13.26 g of water were charged. Nitrogen gas was then introduced into the flask at 20 mL/min; the inside of the flask was stirred at 300 rpm and heated at an ordinary pressure; and the temperature was elevated from 100° C. to 170° C. over 2.0 hours for concentration to obtain a heated concentrate.

Next, with the obtained heated concentrate left in the flask, the inside of the flask was heated at an ordinary pressure while continuing the introduction of nitrogen gas into the flask and stirring; the temperature was elevated to 280° C. over 40 minutes; and furthermore, the temperature was retained at that temperature for about 1.7 hours (100 minutes) to proceed with the cyanation reaction.

After the reaction finished, the reaction product was dissolved in methanol. Furthermore, the catalyst in the solution was removed by filtration and the reaction product was then analyzed by GC (model name "GC-2010 PLUS" manufactured by Shimadzu Corporation, column: product name "HP-5ms" manufactured by Agilent Technologies, 30 m length×0.25 mm i.d., film thickness 0.25 μm, conditions: carrier gas: He (constant pressure: 73.9 kPa), inlet temperature: 300° C., detector: FID, detector temperature: 300° C., column oven temperature: initially 100° C., elevated to 300° C. at 10° C./min, and retained at 300° C. for 10 mins). As a result, the yield of 1,4-dicyanocyclohexane was 2.0%.

Synthetic Example 2-2

In a 100 mL four neck flask equipped with a stirring blade, a gas introduction tube, a thermocouple and a dehydration apparatus, 30.02 g (0.174 mol) of 1,4-cyclohexanedicarboxylic acid, 23.4 g of 28% aqueous ammonia solution (manufactured by Wako Pure Chemical Industry Co., Ltd.), 0.42 g of tin oxide (Wako Pure Chemical Industry Co., Ltd.) as a catalyst and 19.78 g of water were charged. The inside of the flask was then stirred at 300 rpm and heated at an ordinary pressure, and the temperature was elevated from 100° C. to 170° C. over 9.0 hours for concentration to obtain a heated concentrate.

Next, with the obtained heated concentrate left in the flask, the inside of the flask was continuously heated at an ordinary pressure while continuing the introduction of nitrogen gas at 20 mL/min and ammonia gas at 52 mL/min into the flask and stirring; the temperature was elevated to 280° C. over 30 minutes; and furthermore, the temperature was retained at that temperature for 6.5 hours to proceed with the cyanation reaction.

After the reaction finished, the reaction product was dissolved in methanol. Furthermore, the catalyst in the solution was removed by filtration and the reaction product was then analyzed by GC in the same manner as described above. As a result, the yield of 1,4-dicyanocyclohexane was 91.6%.

Synthetic Example 2-3

In a 100 mL four neck flask equipped with a stirring blade, a gas introduction tube, a thermocouple and a dehydration apparatus, 30.03 g (0.174 mol) of 1,4-cyclohexanedicarboxylic acid, 23.51 g of 28% aqueous ammonia solution (manufactured by Wako Pure Chemical Industry Co., Ltd.), 0.24 g of zinc oxide (manufactured by Kanto Chemical Co., Inc.) as a catalyst and 19.78 g of water were charged. The inside of the flask was then stirred at 300 rpm and heated at an ordinary pressure, and the temperature was elevated from 100° C. to 170° C. over 5.7 hours for concentration to obtain a heated concentrate.

Next, with the obtained heated concentrate left in the flask, the inside of the flask was continuously heated at an ordinary pressure while continuing the introduction of nitrogen gas at 20 mL/min and ammonia gas at 52 mL/min into the flask and stirring; the temperature was elevated to 280° C. over 30 minutes; and furthermore, the temperature was retained at that temperature for 6.5 hours to proceed with the cyanation reaction.

After the reaction finished, the reaction product was dissolved in methanol. Furthermore, the catalyst in the solution was removed by filtration and the reaction product was then analyzed by GC in the same manner as described above. As a result, the yield of 1,4-dicyanocyclohexane was 92.9%.

Synthetic Example 2-4

In a 100 mL four neck flask equipped with a stirring blade, a gas introduction tube, a thermocouple and a dehydration apparatus, 30.02 g (0.174 mol) of 1,4-cyclohexanedicarboxylic acid, 23.33 g of 28% aqueous ammonia solution (manufactured by Wako Pure Chemical Industry Co., Ltd.), 0.24 g of zinc oxide (manufactured by Kanto Chemical Co., Inc.) as a catalyst and 13.27 g of water were charged. The inside of the flask was then stirred at 300 rpm and heated at an ordinary pressure, and the temperature was elevated from 100° C. to 170° C. over 1.7 hours for concentration to obtain a heated concentrate.

Next, with the obtained heated concentrate left in the flask, the inside of the flask was continuously heated at an ordinary pressure while continuing the introduction of nitrogen gas at 20 mL/min and ammonia gas at 52 mL/min into the flask and stirring; the temperature was elevated to 300°

C. over 24 minutes; and furthermore, the temperature was retained at that temperature for 6.5 hours to proceed with the cyanation reaction.

After the reaction finished, the reaction product was dissolved in methanol. Furthermore, the catalyst in the solution was removed by filtration and the reaction product was then analyzed by GC in the same manner as described above. As a result, the yield of 1,4-dicyanocyclohexane was 89.2%.

Synthetic Example 2-5

In a 100 mL four neck flask equipped with a stirring blade, a gas introduction tube, a thermocouple and a dehydration apparatus, 30.05 g (0.174 mol) of 1,4-cyclohexanedicarboxylic acid, 23.32 g of 28% aqueous ammonia solution (manufactured by Wako Pure Chemical Industry Co., Ltd.), 0.24 g of zinc oxide (manufactured by Kanto Chemical Co., Inc.) as a catalyst and 13.70 g of water were charged. The inside of the flask was then stirred at 300 rpm and heated at an ordinary pressure, and the temperature was elevated from 100° C. to 170° C. over 1.3 hours for concentration to obtain a heated concentrate.

Next, with the obtained heated concentrate left in the flask, the inside of the flask was continuously heated at an ordinary pressure while continuing the introduction of nitrogen gas at 80 mL/min and ammonia gas at 52 mL/min into the flask and stirring; the temperature was elevated to 280° C. over 27 minutes; and furthermore, the temperature was retained at that temperature for 6.5 hours to proceed with the cyanation reaction.

After the reaction finished, the reaction product was dissolved in methanol. Furthermore, the catalyst in the solution was removed by filtration and the reaction product was then analyzed by GC in the same manner as described above. As a result, the yield of 1,4-dicyanocyclohexane was 94.7%.

Synthetic Example 2-6

In a 100 mL four neck flask equipped with a stirring blade, a gas introduction tube, a thermocouple and a dehydration apparatus, 30.00 g (0.174 mol) of 1,4-cyclohexanedicarboxylic acid, 23.34 g of 28% aqueous ammonia solution (manufactured by Wako Pure Chemical Industry Co., Ltd.), 0.24 g of zinc oxide (manufactured by Kanto Chemical Co., Inc.) as a catalyst and 13.40 g of water were charged. The inside of the flask was then stirred at 300 rpm and heated at an ordinary pressure, and the temperature was elevated from 100° C. to 170° C. over 1.2 hours for concentration to obtain a heated concentrate.

Next, with the obtained heated concentrate left in the flask, the inside of the flask was continuously heated at an ordinary pressure while continuing the introduction of nitrogen gas at 40 mL/min and ammonia gas at 104 mL/min into the flask and stirring; the temperature was elevated to 280° C. over 24 minutes; and furthermore, the temperature was retained at that temperature for 6.5 hours to proceed with the cyanation reaction.

After the reaction finished, the reaction product was dissolved in methanol. Furthermore, the catalyst in the solution was removed by filtration and the reaction product was then analyzed by GC in the same manner as described above. As a result, the yield of 1,4-dicyanocyclohexane was 90.2%.

Synthetic Example 2-7

In a 100 mL four neck flask equipped with a stirring blade, a gas introduction tube, a thermocouple and a dehydration apparatus, 30.03 g (0.174 mol) of 1,4-cyclohexanedicarboxylic acid, 23.34 g of 28% aqueous ammonia solution (manufactured by Wako Pure Chemical Industry Co., Ltd.), 0.42 g of tin oxide (Wako Pure Chemical Industry Co., Ltd.) as a catalyst and 19.78 g of water were charged. The inside of the flask was then stirred at 300 rpm and heated at an ordinary pressure, and the temperature was elevated from 100° C. to 170° C. over 8.2 hours for concentration to obtain a heated concentrate.

Next, with the obtained heated concentrate left in the flask, the inside of the flask was continuously heated at an ordinary pressure while continuing the introduction of nitrogen gas at 20 mL/min and ammonia gas at 52 mL/min into the flask and stirring; the temperature was elevated to 280° C. over 45 minutes; and furthermore, the temperature was retained at that temperature for 8.6 hours to proceed with the cyanation reaction.

A part of the reaction product was taken and dissolved in methanol, and the analysis by GC was performed in the same manner as described above. As a result, the yield of 1,4-dicyanocyclohexane was 95.0%.

Distillation Step

After the reaction finished, the gas introduction tube and the dehydration apparatus were detached from the flask, and a cooler and a receiver were attached to the flask. Next, distillation was performed under conditions where the internal pressure of the flask was 3.5 kPa, the temperature at the bottom section was 199 to 220° C., and the temperature at the top section was 190 to 216.8° C., and 1,4-dicyanocyclohexane was distilled and collected from the top section of the flask. Note that a mantle heater was used for heating the bottom section of the flask. As to the collected 1,4-dicyanocyclohexane, analysis by GC was performed in the same manner as described above. As a result, the yield of 1,4-dicyanocyclohexane was 98.3%.

Synthetic Example 2-8

The nucleus hydrogenation reaction was proceeded in the same manner as Synthetic Example 1-1, obtaining an aqueous ammonia solution including 30.07 g (0.174 mol; 8.0% by mass) of 1,4-cyclohexanedicarboxylic acid. Next, into a 100 mL four neck flask equipped with a stirring blade, a gas introduction tube, a thermocouple and a dehydration apparatus, the aqueous ammonia solution was added appropriately; the inside of the flask was heated at an ordinary pressure while stirring at 300 rpm; and the solution was concentrated at 110° C. over 3.5 hours until the concentration of 1,4-cyclohexanedicarboxylic acid reached 50% by mass. Then, 0.24 g of zinc oxide (Kanto Chemical Co., Inc.) as a catalyst was charged into the four neck flask, and the temperature was elevated from 110° C. to 170° C. over 47 minutes for concentration to obtain a heated concentrate.

Next, with the obtained heated concentrate left in the flask, the inside of the flask was continuously heated at an ordinary pressure while continuing the introduction of nitrogen gas at 20 mL/min and ammonia gas at 52 mL/min into the flask and stirring; the temperature was elevated to 280° C. over 13 minutes; and furthermore, the temperature was retained at that temperature for 6.5 hours to proceed with the cyanation reaction.

A part of the reaction product was taken and dissolved in methanol, and the analysis by GC was performed in the same manner as described above. As a result, the yield of 1,4-dicyanocyclohexane was 88.9%.

Nitrile Hydrogenation Step

Synthetic Example 3-1

In a 100 mL pressure resistant vessel made of SUS316 (shaking type), 1 g of 1,4-dicyanocyclohexane, 3.21 g of meta-xylene and 15 g of liquid ammonia as solvents, and 1.5 g of Raney cobalt catalyst (manufactured by Wako Pure Chemical Industry Co., Ltd.) as a catalyst were charged, and hydrogen gas was introduced until the pressure in the system reached 10 MPa. Then, the inside of the vessel was heated until reaching 80° C., and the vessel was shaken while maintaining the temperature, advancing the nitrile hydrogenation step for 2 hours.

After the reaction finished, ammonia was removed from the reaction solution, and the reaction product was then analyzed by GC (model name "GC-2010" manufactured by Shimadzu Science Co., column: product name "DP-1701" manufactured by Agilent Technologies, 30 m length×0.25 mm i.d., film thickness 0.25 μm, conditions: carrier gas: He (constant pressure: 73.9 kPa), inlet temperature: 300° C., detector: FID, detector temperature: 300° C., column oven temperature: initially 120° C., retained for 5 mins, elevated to 280° C. at 20° C./min, and retained at 280° C. for 5 mins). As a result, the conversion rate of 1,4-dicyanocyclohexane was 99.7%, the selectivity and the yield of 1,4-bis(aminomethyl)cyclohexane were 94.8% and 94.5%, respectively.

Synthetic Example 3-2

In a 300 mL pressure resistant vessel made of SUS316, 24.4 g of 1,4-dicyanocyclohexane, 37.3 g of methanol and 28.4 g of 28% aqueous ammonia (manufactured by Wako Pure Chemical Industry Co., Ltd.) as solvents, and 0.56 g of Raney cobalt catalyst (manufactured by Wako Pure Chemical Industry Co., Ltd.) as a catalyst were charged, and furthermore, hydrogen gas was introduced until reaching a reaction pressure of 4.5 MPa. Next, the inside of the vessel was heated to a reaction temperature of 80° C., and while retaining the constant temperature and stirring the inside of the vessel with an electromagnetic stirring blade at 750 rpm, the nitrile hydrogenation reaction was proceeded for 240 minutes. As a result, the conversion rate of 1,4-dicyanocyclohexane was 100%, the selectivity and the yield of 1,4-bis(aminomethyl)cyclohexane were 97.0% and 97.0%, respectively.

Comparative Example 1

In a 100 mL four neck flask equipped with a stirring blade, a gas introduction tube, a thermocouple and a dehydration apparatus, 30.01 g (0.174 mol) of 1,4-cyclohexanedicarboxylic acid, 0.24 g of zinc oxide (manufactured by Kanto Chemical Co., Inc.) as a catalyst and 30.19 g of water were charged. The inside of the flask was then stirred at 300 rpm and heated at an ordinary pressure, and the temperature was elevated from 100° C. to 170° C. over 1.5 hours for concentration to obtain a heated concentrate.

Next, with the obtained heated concentrate left in the flask, the inside of the flask was continuously heated at an ordinary pressure while continuing the introduction of nitrogen gas at 20 mL/min and ammonia gas at 52 mL/min into the flask and stirring; the temperature was elevated to 280° C. over 25 minutes; and furthermore, the temperature was retained at that temperature for 6.5 hours to proceed with the cyanation reaction.

After the reaction finished, the reaction product was dissolved in methanol. Furthermore, the catalyst in the solution was removed by filtration and the reaction product was then analyzed by GC in the same manner as described above. As a result, the yield of 1,4-dicyanocyclohexane was 51.9%.

INDUSTRIAL APPLICABILITY

According to the present invention, a new method for producing 1,4-dicyanocyclohexane can be provided that enables effective utilization of ammonia. Since 1,4-dicyanocyclohexane can be a raw material for bis(aminomethyl)cyclohexane, which is effective as an optical material for a plastic lens, prism, optical fiber, information recording substrate, filter, etc., used for polyamide, polyurethane and the like, it has an industrial applicability in such fields.

The invention claimed is:

1. A method for producing 1,4-dicyanocyclohexane, comprising:
    obtaining 1,4-dicyanocyclohexane by subjecting a heated concentrate of an aqueous ammonia solution of 1,4-cyclohexanedicarboxylic acid to a cyanation reaction.

2. The method according to claim 1, further comprising:
    obtaining the 1,4-cyclohexanedicarboxylic acid by subjecting terephthalic acid in an aqueous ammonia solution to a hydrogenation reaction.

3. The method according to claim 2, wherein at least a part of an aqueous ammonia solution included in a reaction solution after obtaining 1,4-cyclohexanedicarboxylic acid is used as the aqueous ammonia solution in the obtaining of 1,4-dicyanocyclohexane.

4. The method according to claim 2, wherein the reaction solution after the obtaining of 1,4-cyclohexanedicarboxylic acid is used as a raw material solution for the obtaining of 1,4-dicyanocyclohexane, without collecting 1,4-cyclohexanedicarboxylic acid by filtration therefrom.

5. The method according to claim 1, further comprising obtaining the heated concentrate by heating the aqueous ammonia solution of 1,4-cyclohexanedicarboxylic acid to 100 to 200° C. to remove at least a part of water.

6. The method according to claim 3, wherein the reaction solution after obtaining 1,4-cyclohexanedicarboxylic acid is used as a raw material solution for the obtaining of 1,4-dicyanocyclohexane, without collecting 1,4-cyclohexanedicarboxylic acid by filtration therefrom.

7. The method according to claim 2, further comprising obtaining the heated concentrate by heating the aqueous ammonia solution of 1,4-cyclohexanedicarboxylic acid to 100 to 200° C. to remove at least a part of water.

8. The method according to claim 3, further comprising obtaining the heated concentrate by heating the aqueous ammonia solution of 1,4-cyclohexanedicarboxylic acid to 100 to 200° C. to remove at least a part of water.

9. The method according to claim 4, further comprising obtaining the heated concentrate by heating the aqueous ammonia solution of 1,4-cyclohexanedicarboxylic acid to 100 to 200° C. to remove at least a part of water.

10. The method according to claim 6, further comprising obtaining the heated concentrate by heating the aqueous ammonia solution of 1,4-cyclohexanedicarboxylic acid to 100 to 200° C. to remove at least a part of water.

* * * * *